US006817975B1

(12) United States Patent
Farr et al.

(10) Patent No.: US 6,817,975 B1
(45) Date of Patent: Nov. 16, 2004

(54) ENDOSCOPE

(75) Inventors: Mina Farr, Palo Alto, CA (US);
Wolfgang Braxmeier, Emmendingen (DE)

(73) Assignee: Intuitive Surgical, Inc., Mountain View, CA (US)

( * ) Notice: Subject to any disclaimer, the term of this patent is extended or adjusted under 35 U.S.C. 154(b) by 289 days.

(21) Appl. No.: 09/689,444

(22) Filed: Oct. 12, 2000

Related U.S. Application Data

(63) Continuation-in-part of application No. 09/680,922, filed on Oct. 6, 2000, now abandoned.
(60) Provisional application No. 60/176,101, filed on Jan. 14, 2000.

(51) Int. Cl.[7] .............................................. A61B 1/002
(52) U.S. Cl. ..................... 600/160; 600/138; 600/162; 600/166; 359/434
(58) Field of Search ............................... 600/138, 162, 600/166, 160; 353/434, 435

(56) References Cited

U.S. PATENT DOCUMENTS

| 4,723,843 A | 2/1988 | Zobel |
| 4,903,133 A | 2/1990 | Hiltebrandt |
| 4,969,708 A | 11/1990 | Leiner |
| 5,078,503 A | 1/1992 | Ueda |
| 5,449,422 A | 9/1995 | Pflanz et al. |
| 5,459,605 A | 10/1995 | Kempf |
| 5,519,532 A * | 5/1996 | Broome ..................... 359/435 |
| 5,527,263 A | 6/1996 | Zobel et al. |
| 5,588,948 A | 12/1996 | Takahashi et al. |
| 5,720,706 A | 2/1998 | Takahashi et al. |
| 5,743,846 A | 4/1998 | Takahashi et al. |
| 5,764,809 A | 6/1998 | Nomami et al. |
| 5,776,049 A | 7/1998 | Takahashi |
| 5,833,596 A * | 11/1998 | Bonnell et al. ............. 600/109 |
| 5,842,972 A | 12/1998 | Wulfsberg |
| 5,852,511 A | 12/1998 | Tateyama et al. |
| 5,860,912 A | 1/1999 | Chiba |
| 5,912,764 A | 6/1999 | Togino |
| 5,980,453 A | 11/1999 | Forkey et al. |

* cited by examiner

Primary Examiner—John P. Leubecker
(74) Attorney, Agent, or Firm—Townsend and Townsend and Crew LLP

(57) ABSTRACT

Improved optical devices and methods transmit optical images along elongate optical paths with relatively limited cross-sectional dimensions using an improved objective, relay, and ocular systems. In a first aspect, at least one intermediate image formed within an optical component, rather than being formed in a gap between optical components. In a preferred embodiment, a first intermediate image is formed within glass of the most proximal objective lens, with the first intermediate image extending axially along a curved image location within the glass. The last intermediate image may similarly be disposed within a distal lens of the ocular system. By making use of a first and/or last intermediate image disposed in this manner within a lens, endoscopes can exhibit a significantly larger Numerical Aperture than known endoscopes having similar cross-sectional dimensions. In a second aspect, the ocular system allows independent adjustment of diopters, magnification, X-Y positioning, and rotation orientation of the captured image while introducing minimal aberrations.

30 Claims, 14 Drawing Sheets

ENDOSCOPE

CROSS REFERENCE TO RELATED APPLICATIONS

The present application claims the benefit under 35 U.S.C. Section 119(e) of U.S. Privisional Patent Application No. 60/176,101, filed Jan. 14, 2000, entitled "Endoscope Relay," and is a continuation-in-part of U.S. patent application Ser. No. 09/680,922, filed Oct. 6, 2000 now abandoned, entitled "Endoscope", the complete disclosures of which are incorporated herein by reference.

BACKGROUND OF THE INVENTION

1. Field of the Invention

The present invention is generally related to optical devices and methods such as those used for surgery. In particular the present invention relates to techniques for enhancing the throughput and manipulation of optical information through a limited cross-section endoscopic relay. In one aspect, the invention provides an endoscope having an optical relay, objective, or ocular using at least one intermediate image formed within an optical component such as a glass element or lens. In another aspect, the invention provides an ocular system that permits independent adjustment of the diopters, magnification, X-Y positioning and rotational orientation of an image, while introducing minimal aberrations.

Minimally invasive medical techniques are aimed at reducing the amount of extraneous tissue which is damaged during diagnostic or surgical procedures, thereby reducing patient recovery time, discomfort, and deleterious side effects. The average length of a hospital stay for a standard surgery is significantly longer than the average length for the equivalent surgery performed in a minimally invasive surgical manner. Patient recovery times, patient discomfort, surgical side effects, and time away from work are also reduced with minimally invasive surgery.

The most common form of minimally invasive surgery may be endoscopy. Probably the most common form of endoscopy is laparoscopy, which is minimally invasive inspection and surgery inside the abdominal cavity. In standard laparoscopic surgery, a patient's abdomen is insufflated with gas, and cannula sleeves are passed through small (approximately ½ inch) incisions to provide entry ports for laparoscopic surgical instruments.

The laparoscopic surgical instruments generally include a laparoscope for viewing the surgical field, and working tools defining end effectors. To perform surgical procedures, the surgeon passes these working tools or instruments through cannula sleeves to a desired internal surgical site and manipulates the tools from outside the abdomen. The surgeon often monitors the procedure by means of a television monitor which displays an image of the surgical site via the laparoscopic camera. Similar endoscopic techniques are employed in, e.g., arthroscopy, retroperitoneoscopy, pelviscopy, nephroscopy, cystoscopy, cisternoscopy, sinoscopy, hysteroscopy, urethroscopy, and the like.

Minimally invasive telesurgical systems are now being developed to increase a surgeon's dexterity, so that the surgeon performs the surgical procedures on the patient by manipulating master control devices to control the motion of servomechanically operated instruments. In such a telesurgery system, the surgeon is again provided with an image of the surgical site via an endoscope. In both telesurgical and manual endoscopic procedures, the endoscope may optionally provide the surgeon with a stereoscopic image to increase the surgeon's ability to sense three-dimensional information regarding the tissue and procedure.

Endoscopes typically include three optical sub-systems: an objective lens system, an ocular lens system, and a relay lens system. The objective lens system is located at the distal portion of the endoscope to capture the desired image. The ocular lens system or eyepiece is located at the proximal portion of the endoscope and generally remains outside the patient body to transmit the desired image to the eye, camera, or the like. The relay lens system is generally disposed between the objective and ocular to transfer the image proximally out of the patient along a relatively small diameter endoscope shaft.

The objective lens system is typically separated from the relay system by an objective-relay air gap, while the relay system is separated from the ocular lens system by a relay-ocular air gap. The relay will typically be separated into a series of relay lens units, with the relay units again being separated by gaps. The objective lens system generally forms a first intermediate image in the objective-relay gap. The relay lens system then transfers this intermediate image from the distal portion of the scope toward the proximal portion by generating as many intermediate relay images as appropriate to travel the length of the shaft. A last intermediate image is produced by the relay system in the relay-ocular gap. The ocular collimates or nearly collimates this final intermediate image for detection by a surgeon's eye via viewing lenses such as an eyepiece, or for transmission to the imaging optics of a camera, the camera optics typically forming a final image on a charge couple device (CCD) of the camera.

The ocular lens system of known monoscopic endoscopes typically has a plurality of lenses that can manipulate the captured image. The optical properties of the captured image can be modified to ensure proper viewing of the desired object within the body. While such adjustments may be adequate for monoscopic endoscopes, when imaging a target site with a stereo imaging optics, it is of particular importance to have very accurate adjustments between the stereo channels to provide accurate three dimensional information that can be matched between the two channels. If accurate matching is not accomplished, the stereo viewer will provide an inaccurate image and may cause eye strain for the user.

While these known monoscopic endoscopic structures and methods have been quite successful, and are now widely used for imaging of internal tissues and surgical sites via minimally invasive apertures, further improvements would be desirable. In general, it would be desirable to provide improved optical systems and methods. It would be particularly desirable if these improved optical techniques enhanced the amount of optical information which could be transmitted along an optical path having a given, relatively limited cross-section (and/or diminished the cross-section to transmit a given image). It would further be desirable to provide improved monoscopic and stereoscopic endoscopes with enhanced image quality and/or decreased cross-sectional dimensions for use in manual and robotic minimally invasive surgical procedures. Additionally, it would further be desirable to provide an ocular system which allows independent adjustment of the optical properties of the image, while limiting the amount of aberrations introduced. Moreover, it would further be desirable to provide endoscopes which have the sensitivity in its adjustments to allow matching (e.g., position, orientation, size, and simultaneous focus) of the left and right channels of a stereo endoscope.

2. The Background Art

The following U.S. Patents may be related to the present invention, and the full disclosures of each is hereby incorporated herein by reference: U.S. Pat. Nos. 5,568,312; 5,743,846; 5,743,847, 5,776,049; 5,861,987; and 5,956,179.

Robotic surgical systems which might make use of the improved imaging capabilities of the present invention are described in the following U.S. Patent Application Numbers, each of which is incorporated herein by reference: Ser. No. 09/378,173; filed Aug. 20, 1999; Ser. No. 09/433,120, filed Nov. 3, 1999; and Ser. No. 09/418,726, filed Oct. 15, 1999.

SUMMARY OF THE INVENTION

The present invention generally provides improved optical devices and methods for transmitting optical images along elongate optical paths with relatively limited cross-sectional dimensions, particularly for use in surgical endoscopes, boroscopes, periscopes, monoscopes, stereoscopes, and the like.

In one embodiment, the invention provides an endoscope having an objective, relay, and ocular lens system which have at least one intermediate image formed within an optical component, rather than being formed in a gap between optical components. Optical components will herein be used to mean a single lens, a compound lens, a rod lens, a glass element, or other optical elements which have a refractive index of greater than one. The optical component may or may not have surface contours. For example, if the intermediate image is formed in glass, the glass can act to prevent external elements, such as dust, from introducing aberrations into the image.

In an exemplary embodiment, the image-containing optical component will often be a lens within an integrally designed objective-relay (and/or relay-ocular) system. In contrast to standard endoscope systems, which rely on modular, independent designs for their objective lens systems, relay lens systems, and ocular lens systems, the optical train of the present invention need not form a highly corrected intermediate image at an image plane disposed between the objective and relay, and/or between the relay and ocular.

In a preferred embodiment, an intermediate image is formed within the glass of the most proximal objective lens, which extends proximally of the first intermediate image to a proximal surface adjacent the relay. Additionally, this intermediate image will often be allowed to distort or extend significantly along the optical axis (i.e., have a large field curvature) so as to define a curved image location within the glass. A final intermediate image may similarly be disposed within a distal lens of the ocular system. Other intermediate images may be formed in an optical element or gap within the relay lens system.

Surprisingly, by making use of a first and/or last intermediate image disposed within a lens of an integrally designed optical train, the endoscopes of the present invention will generally provide a significantly larger Numerical Aperture than known endoscopes having similar cross-sectional dimensions and length. Consequently, the optical train will produce a highly aberration corrected image with a better image resolution. Forming these intermediate images within glass also decreases the sensitivity of the image quality to dust and/or scratches, which further enhances the viewer's ability to detect small details in the image.

In contrast to known endoscopes, which balance or correct the image at the objective lens system and ocular lens system independently, the endoscopes of the present invention will typically deliver a distorted or unbalanced image from the objective lens system through the relay lens system to the ocular lens system. After the distorted image has been delivered to the ocular lens system, the aberrations in the distorted image are balanced and compensated by the ocular lens system to produce the final image. By delivering an expanding, unbalanced, and distorted image to the ocular lens system, the endoscopes of the present invention are able to achieve a larger throughput relative to conventional endoscopes having the same cross section and length of endoscope, while at the same time reducing the amount of aberrations introduced into the image throughout the optical train. Consequently, a brighter, clearer final image can be created.

In one aspect, the invention provides an optical train for viewing an object. The optical train comprises an objective lens system for acquiring an image of the object and an ocular lens system for forming a final image of the object. A relay lens system is disposed along an optical path between the objective lens system and the ocular lens system. At least one of the objective lens system, relay lens system, and ocular lens system includes an optical element. An intermediate image is formed within the optical element.

Causing an image to coincide with an optical element instead of air, increases the ability of the optical train to image a particular object and causes the optical train to behave as if it had a much larger Numerical Aperture. The invention also permits the image to be less affected by dust or scratches on lens surfaces that would normally harm the image's quality and so affect the viewer's ability to detect small details in the image.

Optionally, the image-containing optical element may be a part of the objective lens system. Although the relay lens system may be separated from the objective lens system by an objective-relay gap, no intermediate image will typically be formed within the objective-relay gap. Alternatively or additionally, the first image-containing optical element may be a part of the ocular lens system, and similarly, no intermediate image need be disposed within an ocular-relay gap. Preferably, first and last intermediate images will be formed within the image-containing optical elements of the objective and ocular lens systems, respectively. The relay system may comprise a plurality of axially separated relay units, with the number of relay units being selected to transmit the image along the desired axial length. Such relay units may be uniform and interchangeable, with each relay unit including an axially symmetric set of relay lenses and glass elements. Additionally, glass elements may be disposed adjacent relay lenses such that other intermediate images are formed in the glass element. Additionally or alternatively, relay gap may be disposed between adjacent relay units so that an associated relay intermediate image is formed therein.

In another embodiment, the invention provides an endoscope comprising a shaft having a distal portion adjacent a distal end and a proximal portion adjacent a proximal end. An ocular lens system is disposed along the proximal portion, and a relay lens system is disposed along the shaft between the proximal portion and the distal portion. An objective lens system is disposed along the distal portion, with the objective lens system comprising an optical element. The objective lens forms a first intermediate image within the optical element.

In yet another embodiment, the invention provides an endoscope for presenting an image of an object to an eye of an observer. The endoscope comprises a scope body having a proximal portion adjacent a proximal end, and a distal portion adjacent a distal end, with an optical path therebetween. An objective lens system is disposed adjacent the distal portion for accepting light from the object and transmitting the light proximally. The objective lens system has an optical element with a distal surface and a proximal surface, and defines a first intermediate image of the object between the surfaces of (and within) the optical element. An ocular lens system is disposed adjacent the proximal portion for viewing the image with the eye adjacent thereto. A relay lens system is disposed between the objective and ocular lens systems, the relay system comprises a plurality of axially separated relay units.

The relay units can be interchangeable and each relay unit can comprise glass elements and an axially symmetric set of relay lenses. In some configurations, a relay gap is disposed between each pair of adjacent relay units so that an associated relay intermediate image is formed in the relay gap. In other configurations, the intermediate image is formed in the glass element. The relay lens system typically has a proximal lens with a proximal surface and a distal lens with a distal surface, and defines at least one intermediate relay image of the object between the proximal and distal lenses of the relay system.

In another aspect, the present invention provides a method of manipulating an image captured by a stereoscopic endoscope. A diopters of the captured image is set. The magnification of an image is independently altered without significantly affecting the diopters. The X-Y positioning of the image is adjusted without introducing aberrations or affecting the diopters and magnification, and an orientation of the captured image is rotated such that the rotation of the image does not affect the diopters, magnification, and X-Y positioning of the captured image.

In still another aspect, the present invention provides a method of manipulating an image within a stereoscopic endoscope which has a first lens, second lens, a third lens, and a prism positioned in an optical path of the ocular system. The method includes moving the lenses of the ocular system along the optical path to adjust a diopters of the endoscope. The position of the first lens is maintained while the second and third lens are moved to adjust the magnification of the image. An orthogonal position of the second lens is adjusted to adjust the X-Y position of the image. The prism is rotated to adjust the rotational orientation of the image.

In a further aspect, the present invention provides a stereoscopic endoscope. The endoscope includes a first channel having a first optical path and a first objective lens system optically coupled to a first ocular lens system through a first relay system. A second channel having a second optical path and a second objective lens system optically coupled to a second ocular lens system through a second relay system is positioned adjacent to the first channel. The first ocular lens system and the second ocular lens system each comprise a first and second positive lens and a negative lens disposed in the optical paths. The negative lenses can be moved off the optical paths so as to stereo match the first channel with the second channel.

The X-Y positioning of the image can be adjusted so that there are reduced (less than 1%) aberrations introduced into the diopters and magnification. The orientation of the captured image can also be independently adjusted without affecting the diopters, magnification, or X-Y positioning of the image.

In yet another aspect, the present invention provides a method of manipulating an image. The method includes capturing an image with an objective lens system. An unbalanced image is relayed through a relay lens system to an ocular lens system. The relay (unbalanced) image is balanced within the ocular system to produce the final image.

In many configurations, the unbalanced image is distorted and expanding. Such a configuration therefore can provide the maximum throughput of optical information through the lens systems. This permits better image resolution and improved image brightness, relative to a conventional lens systems in which the objective and ocular systems are independently balanced.

In still another embodiment, the present invention provides a stereoscopic endoscope. The endoscope includes a shaft having an objective lens system positioned on a distal end of the shaft. A relay lens system is disposed in the shaft, proximal of the objective lens system. An ocular lens system is coupled to a proximal end of the shaft and includes a prism having a wedge at a proximal end for bending light rays to create a stereo line of convergence.

These and other aspects of the invention will be further evident from the attached drawings and description of the embodiments of the invention.

DETAILED DESCRIPTION OF THE SPECIFIC EMBODIMENTS

While the invention will generally be described herein with reference to surgical optical imaging devices and methods, the invention has applications for any lens systems that transfer optical information through a relay (a series of small diameter lenses) such as, for example, monoscopes, stereoscopes, boroscopes, periscopes, arthroscopes, and the like.

Figure 1:
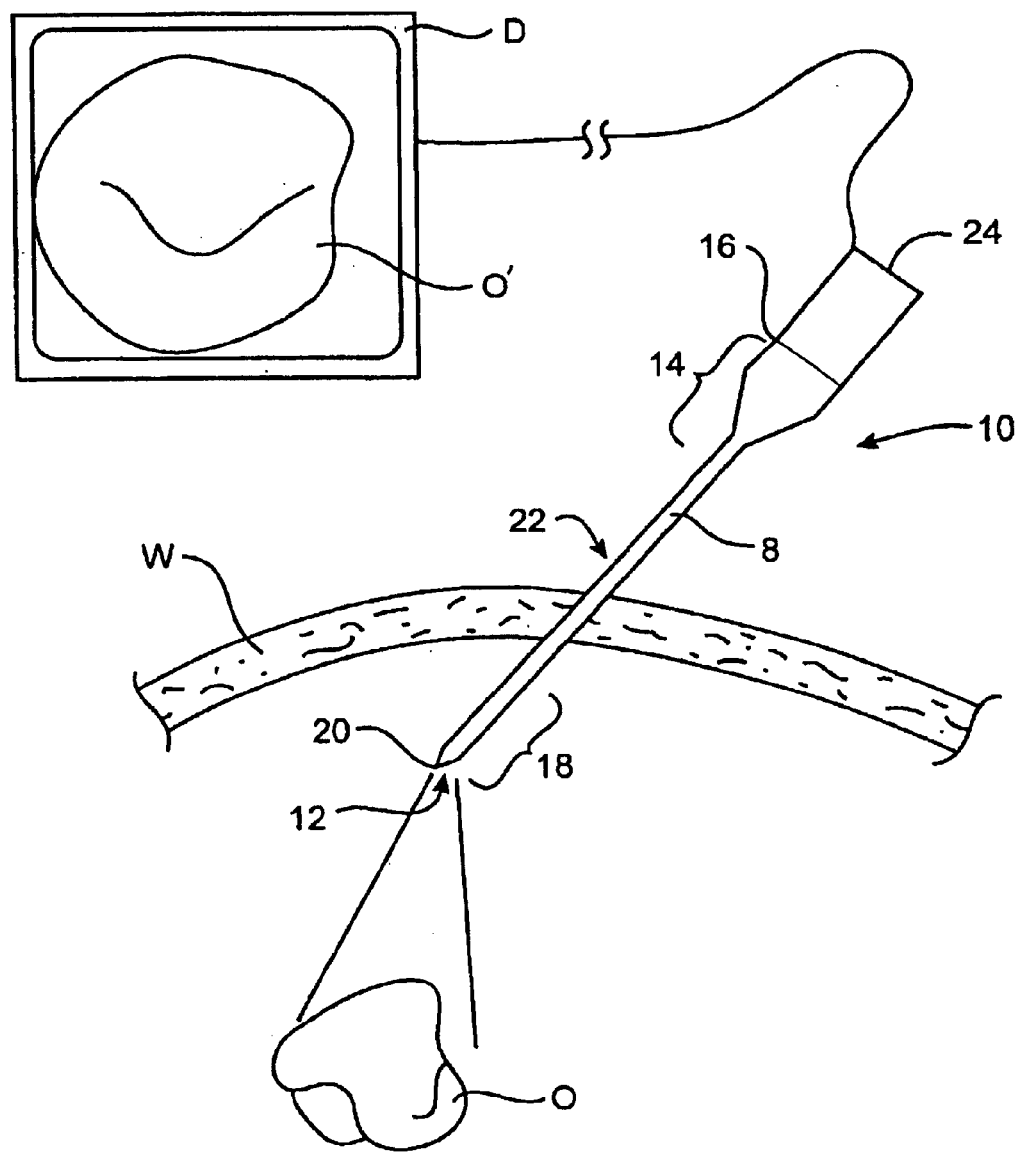
FIG. 1 schematically illustrates an endoscope and a method for its use according to the principles of the present invention.

Referring now to FIG. 1, an endoscope 10 extends through a body wall W to an internal viewing site within a patient body. Endoscope 10 includes a shaft or body 8 containing an optical train 12. Endoscope 10 generally has a proximal portion 14 adjacent a proximal end 16, a distal portion 18 adjacent a distal end 20, and an intermediate portion 22 between the proximal and distal portions.

In use, an object O is within a field of view of endoscope 10, which transmits an image of the object O' proximally to a camera 24 optically coupled to proximal end 16 of the endoscope. Camera 24 will typically have a charge-couple device (CCD) or the like, so that the camera can transmit image signals to allow a display D to reproduce the image O'. The field of view may optionally be angled relative to shaft 8, and the endoscope 10, camera 24, and display D may be arranged to provide a stereoscopic view to a system operator, as more fully explained in co-pending U.S. patent application Ser. No. 09/378,173, which was previously incorporated herein by reference.

Figure 2:
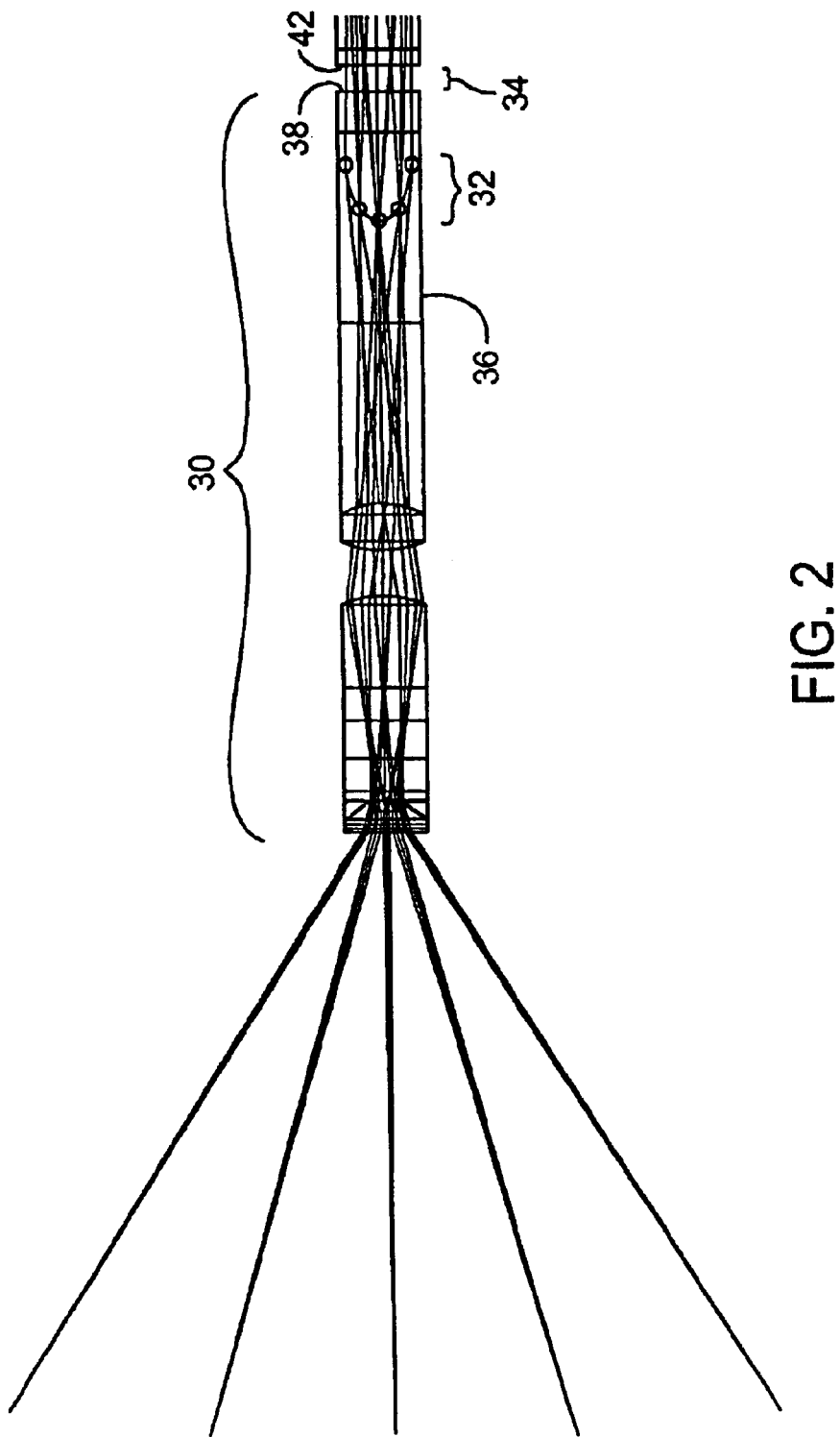
FIG. 2 illustrates the optical components of an objective lens system along a distal portion of the endoscope of FIG. 1.
Figure 3:
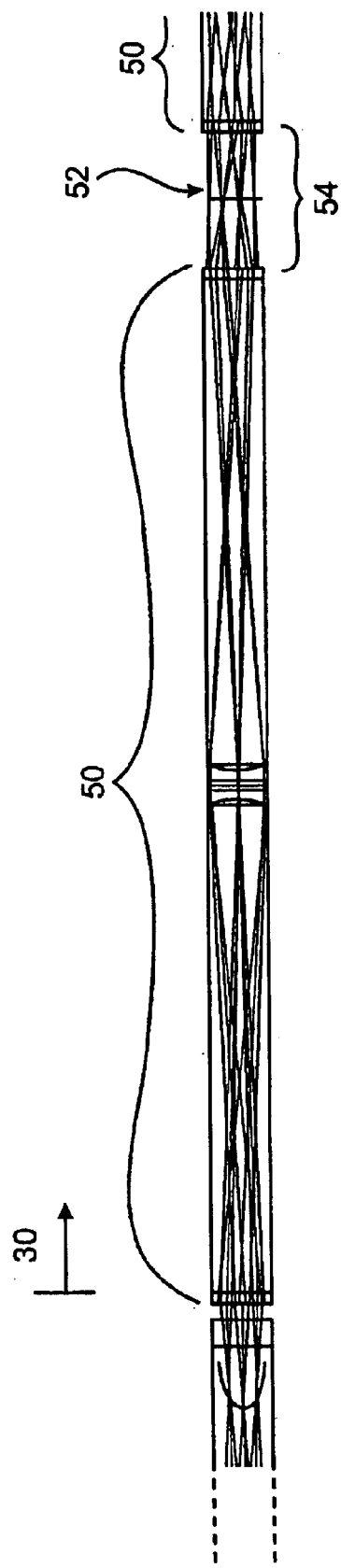
FIG. 3 illustrates the optical components of a relay lens system along an intermediate portion of the endoscope of FIG. 1.
Figure 4:
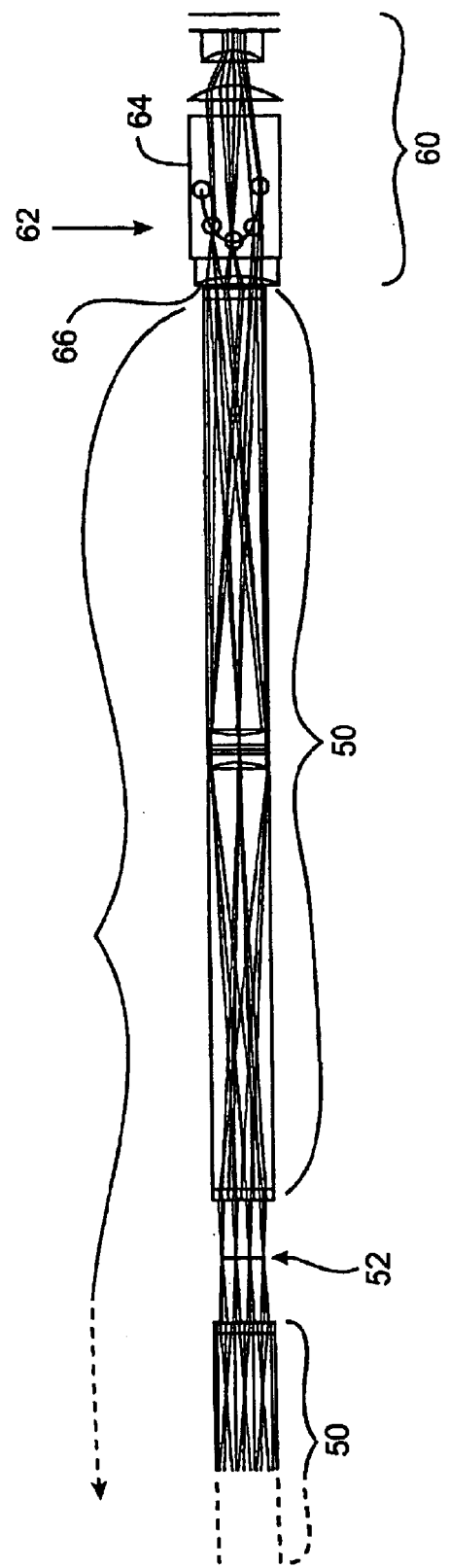
FIG. 4 illustrates a proximal portion of the relay and a distal portion of the optical components of an ocular lens system.
Figure 5:
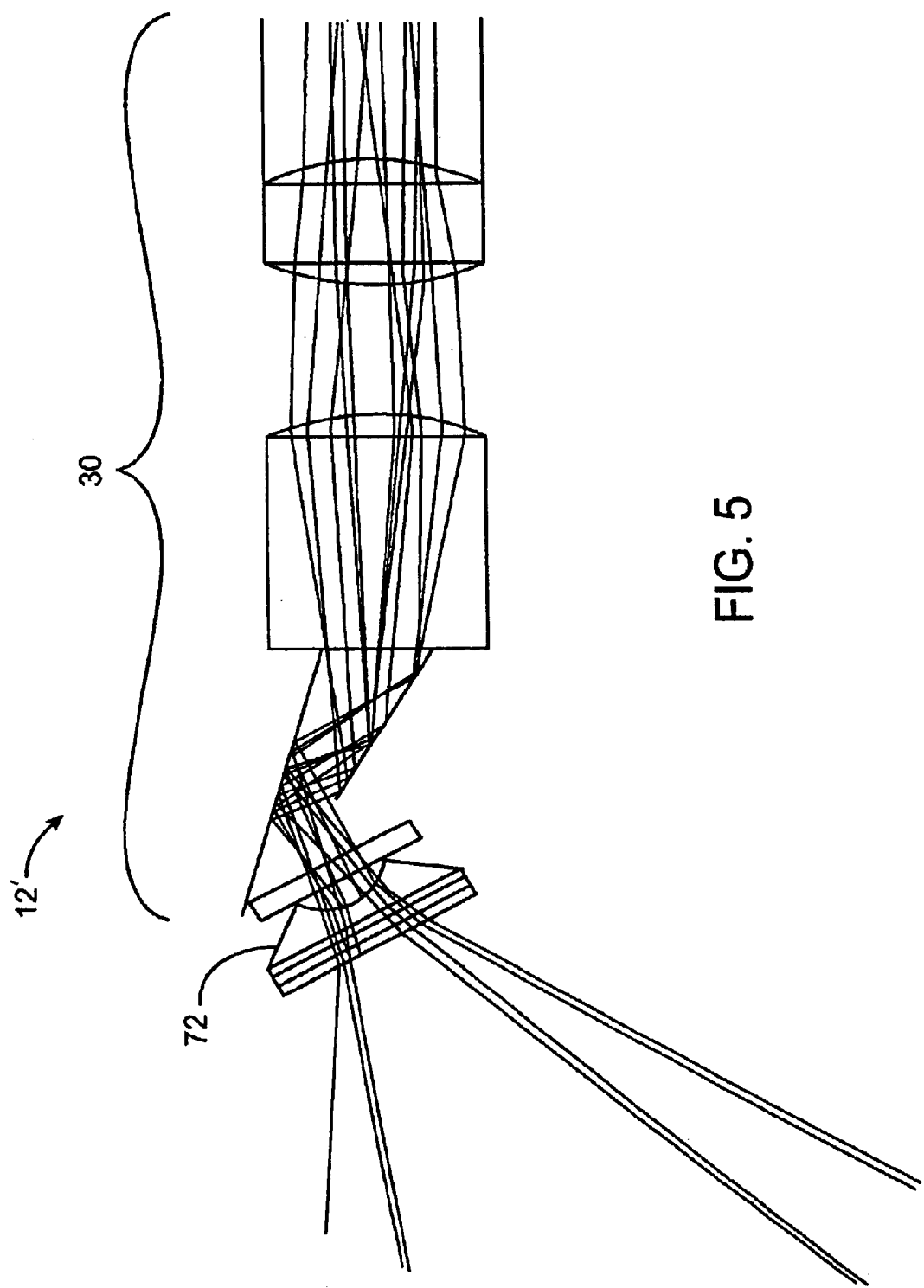
FIG. 5 illustrates an objective lens of the present invention.
Figure 6:
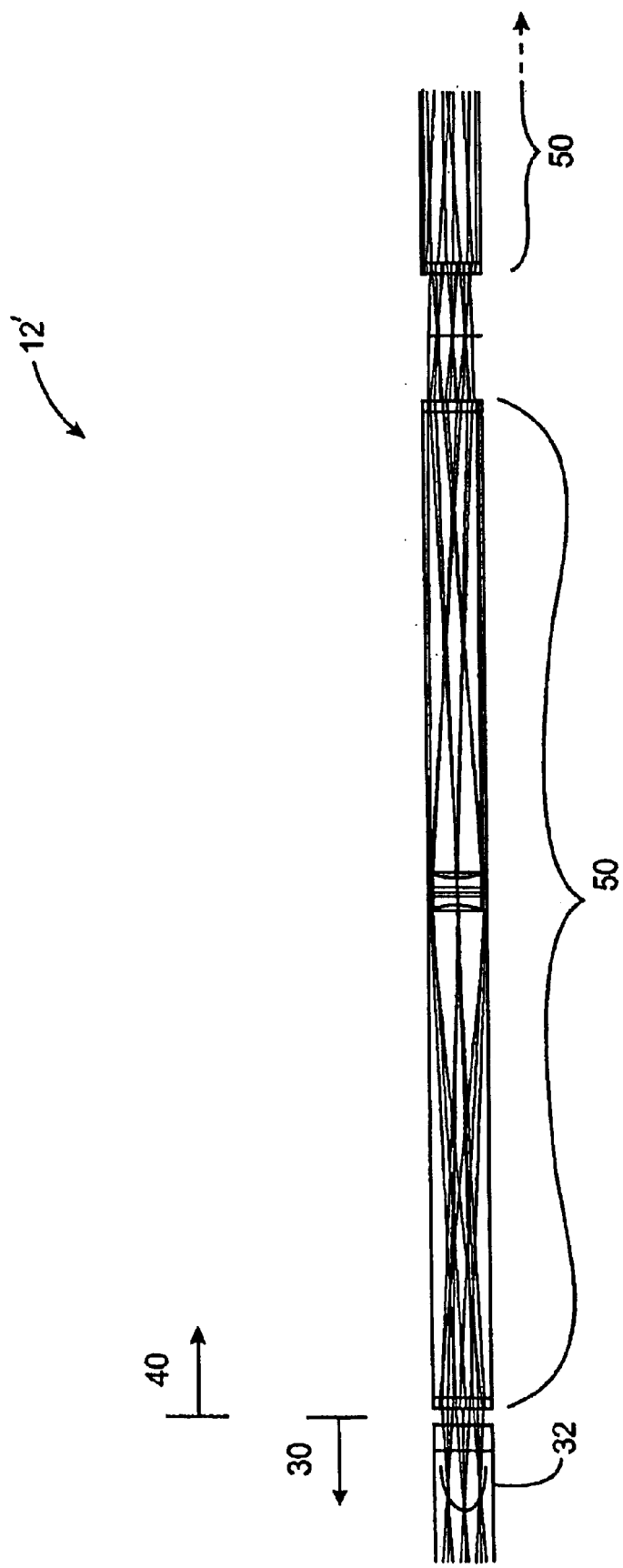
FIG. 6 illustrates a distal portion of the relay.
Figure 7:
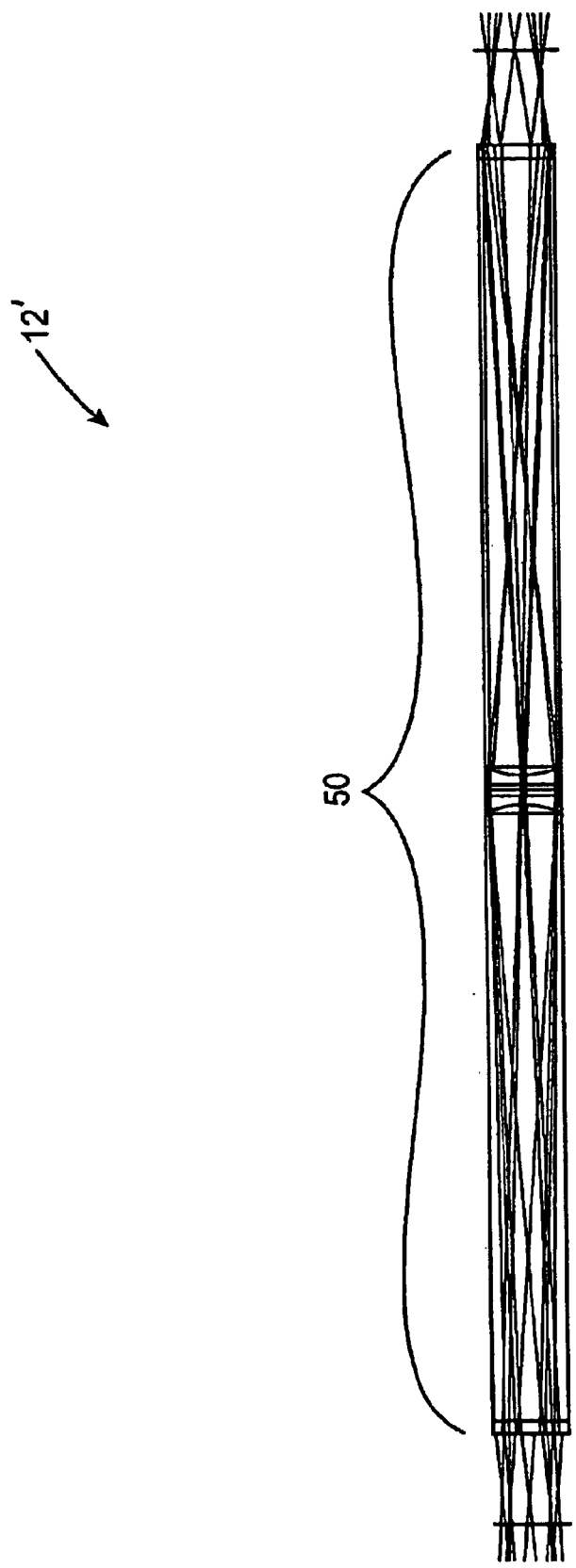
FIG. 7 illustrates an intermediate portion of the relay.
Figure 8:
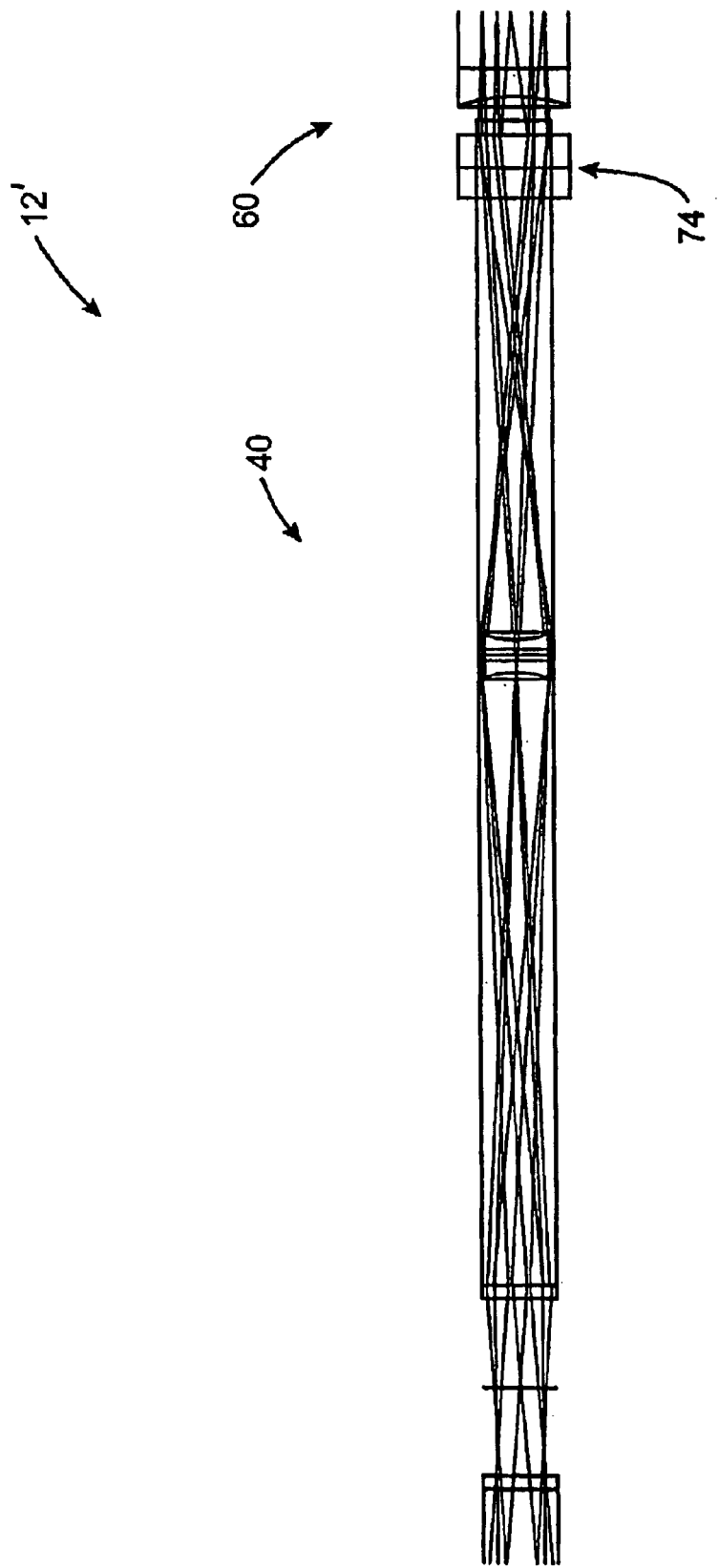
FIG. 8 illustrates a proximal portion of the relay and a distal portion of the ocular.
Figure 9:
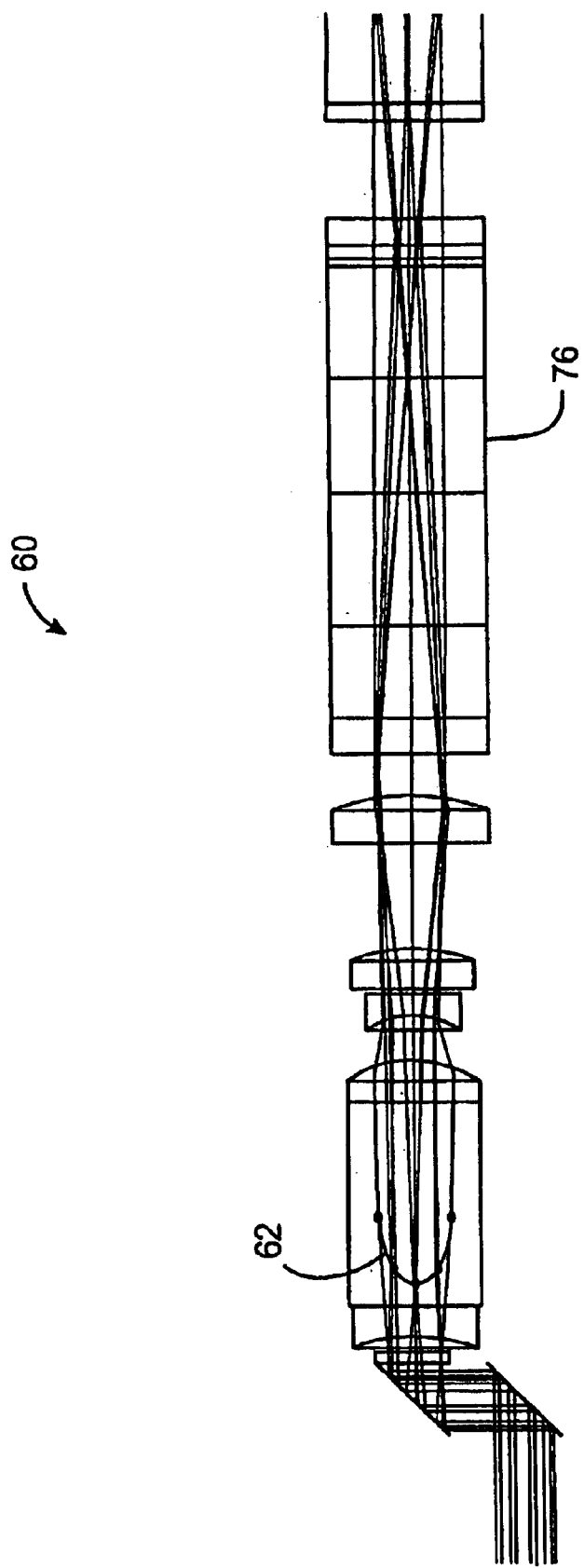
FIG. 9 illustrate the stereoscopic separation in the proximal portion of the relay, distal of the ocular system.
Figure 10:
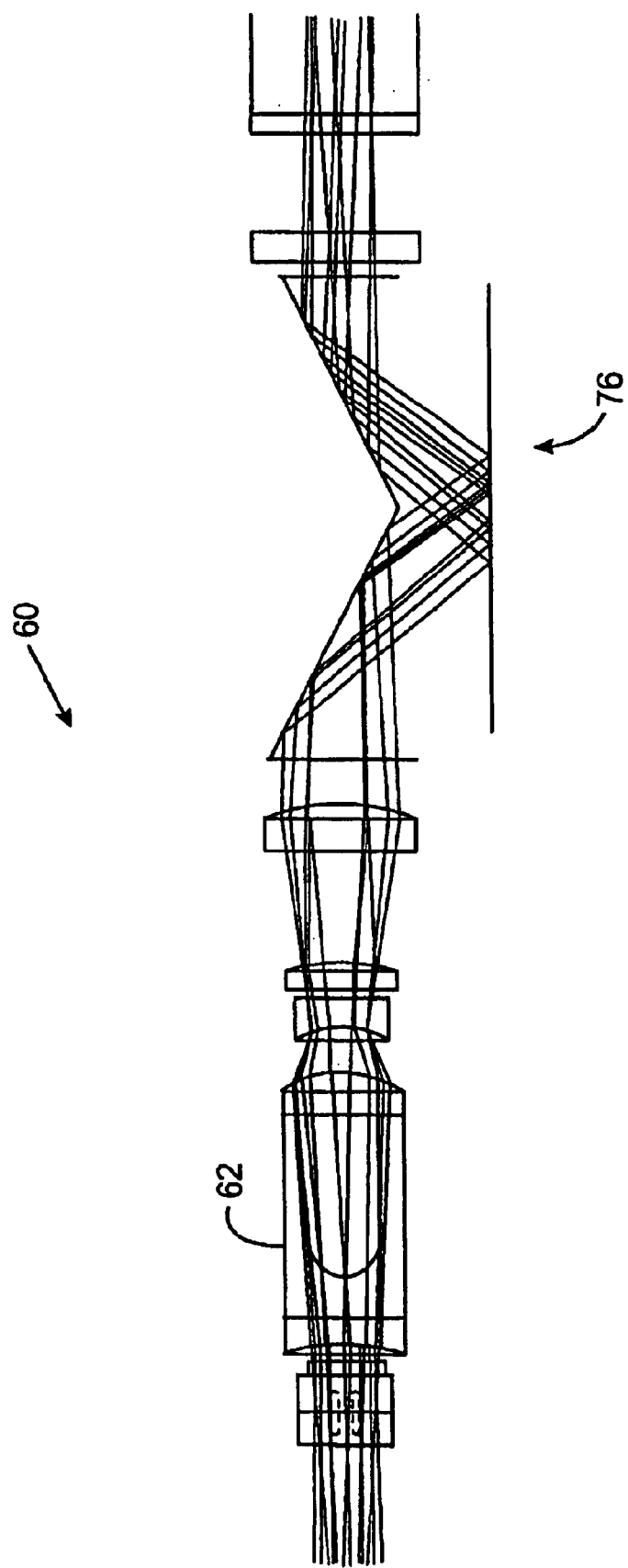
FIG. 10 is a lateral view of the proximal portion of the embodiment of FIG. 9, illustrating the operation of a prism of the ocular optical lens system.

Optical train 12 of endoscope 10 will generally include three lens systems: an objective lens system 30 in distal portion 18 (seen most clearly in FIG. 2), a relay lens system 40 in intermediate portion 22 (which will typically comprise a number of relay units 50, and which is seen most clearly in FIGS. 3 and 4), and an ocular lens system 60 (shown in FIGS. 4 and 10).

In standard monoscopic and stereoscopic endoscopes, the objective, relay, and ocular lens systems are typically designed independently and modularly, in the sense that the objective is designed to produce a first discrete image at a specific image point, the relay is designed to form a second at a second image point, and the ocular is designed to take the second image and manipulate it for viewing by a user. The invention merges the design of the objective-relay-ocular lens system, objective and ocular designs, the objective and relay lens systems, and/or the design of the relay and ocular lens systems.

For every optical system, including an endoscope, according to the principles embodied in the Lagrange Invariant or Optical Invariant, the product (h)(NA)=a constant, dictated by the particular geometry (length, diameter, number of relays) of the endoscope/relay. This equation represents the limited ability of the endoscope/relay to collect and transfer image information. This product of h and NA remains constant for any location in an endoscope, where h=height of the given image, and NA is the endoscope's Numerical Aperture at the location of the image along the endoscope. {Note: NA=[(index of refraction of the medium in which the image is present)× (sine [Theta])], where Theta is the angle between the chief and marginal rays from the image. ("Marginal ray" is the ray passing from the image through the edge of the aperture stop.)}

Thus, according to this equation, as the image size increases, the effective NA of the endoscope shrinks, to keep the (h)(NA) endoscope throughput constant. Typically, the NA value is limited so as to avoid vignetting of the off-center axis portions of the image. Thus, the NA of an endoscope typically is not determined by the extent of the first relay lens aperture but rather by the aperture size inside the relay.

This (h)(NA) product—which may also be referred to as the endoscope's "image information throughput"—provides a measure of the quality of image achievable with a particular endoscope. Aberrations in the image can limit the effective (h)(NA) product. The present invention enhances the product of (h)(NA)—either increasing the possible NA for a fixed h, or increasing the image size h capable of being throughputted for a fixed NA—and so increases the clarity of a given size image (of the object) produced at the proximal end of the endoscope. In short, the present invention results in the product (h)(NA) higher than previous endoscopes.

As illustrated in FIGS. 2–4, unlike typical endoscopes, endoscope 10 has an objective 30 constructed in such a way that a first intermediate image 32 falls not within an air space 34 between the objective and the relay 50. In the preferred embodiment, this first intermediate image 32 falls within the glass of the most proximal objective lens 36 which is extended proximal of the position of the first intermediate image 32 and into close proximity to the distal most surface 42 of relay 40.

Causing the first intermediate image to coincide with glass instead of air, by, e.g., extending the most proximal objective lens portion, increases the ability of the endoscope to image a particular object and causes the endoscope to behave as if it had a much larger Numerical Aperture. The invention also permits the image to be less affected by dust or scratches on lens surfaces that would normally harm the image's quality and so affect the viewer's ability to detect small details in the image.

As illustrated in the FIG. 2, the first intermediate image 32 is formed before the light rays have ceased expanding to their most extreme off-axis location (typically the endoscope's diameter). Because the light rays in the objective are still expanding when the image is formed, a larger image than that of a known endoscope is formed. However, because the light rays of the image are still expanding, it is desirable to cause the rays to converge (i) as if emanating from a larger object, and (ii) sufficiently so that all the light remains within the relay and no image information is lost. The most proximal objective lens surface 38 preferably serves this purpose.

Because no intermediate image is required to be formed in any space between the objective and relay lenses (e.g., space 34), the most proximal surface 38 of the objective system 30 can be positioned very closely to the most distal surface 42 of the relay 40. The dimensions of the gap may be a function only of the desired curvature of the proximal most objective surface 38, which is curved sufficiently to preferably cause all of the light rays from the object and intermediate image to remain in the endoscope and not be lost. Due to the difference in index of refraction between glass and air and because of the curvature of that particular lens, the most proximal objective lens bends the light back into the endoscope. Thus, the endoscope's ability to carry an increased image size (formed form the still-diverging light rays in the objective) is improved. The curvature of the proximal most portion 38 of the objective and the particular index of refraction of the glass are chosen to balance the aberrations of the entire optical system and so enable successful transmission of the image through the relay 40 to the eyepiece.

To maximize the benefits of the present invention, the extreme off axis rays of the image will preferably converge at points distal of the element capable of converging the still-diverging rays into relay 40. This task preferably is achieved with a combination of the curvature of the proximal-most face of the objective lens 38 in combination with the difference in refractive index between the glass of the objective lens and the air between the objective lens and relay lens. Were any of the ray sets of the present invention to form an image after this most proximal objective lens face 38 the rays would not converge sufficiently to all be capturable by the relay 40. This converging function can also be performed by other optical elements, as would be obvious to one of skill in the art upon reading this disclosure, such as other glass or materials with a different refractive index.

The exemplary endoscope 10 has a shaft diameter of about 5 mm, a length of about 400 mm, and 4 sets of relay rod lens units 50. Note that the (NA)(h) product that can pass through the relay is also dependent on the length of the relay. Thus, it is easier to pass an intermediate image having a large size through shorter endoscope relays without introducing aberrations. As the relay length gets longer, however, with the increase in relay lenses, there is a greater chance of introducing aberrations. Improvements in intermediate image size have been demonstrated from about 1.5 mm off-axis (for a known endoscope relay arrangement) to about 2 mm off-axis (or about a 33% increase in image size for the inventive endoscope) without modifying the numerical aperture of the scope shaft 8 or the length of the relay. In other words, the image passed through the endoscope has been magnified while maintaining a constant NA. Thus, for the preferred embodiment of the present invention, the endoscope's throughput, (h)(NA), for a constant NA, has increased by as much as 33%, providing a resulting image with 33% greater resolution over conventional endoscopes. Consequently, the objective system of the present invention can have a larger (NA)(h) product so as to pass more of the image through the same length endoscope. Of course, for other geometries of endoscope (e.g., different diameters, different lengths and/or different relay arrangements, etc.) the present invention permits an intermediate image having a larger size (and thus a larger information throughput through a certain length of relay) than is otherwise possible with known designs, perhaps by greater than 33%.

The practical effect of increasing the throughput of information through an endoscope by increasing the value of the product (h)(NA) is to increase the amount of information about the object provided to the observer, thereby providing better image resolution and improved image brightness.

Referring now to FIG. 4, which shows a proximal portion of the relay unit 50 and a distal portion of the ocular system 60, a last intermediate image 62 is formed within glass of a lens 80 (shown in FIG. 10) of ocular system 60, thereby providing an alternative manner of correcting for distortions and field curvature and increasing the size of the image carried by the ocular portion of the endoscope. Ocular system 60 effectively corrects for different image aberrations such as distortion and field curvature without the use of optical components that would otherwise impair the performance or manufacturability of the endoscope.

In the preferred embodiment illustrated in FIGS. 4 and 10, the last intermediate image 62 of the relay 50 is caused to coincide with the most distal, extended ocular lens 80 instead of in an air gap, as in image 52 between adjacent relay units 50. The most distal surface 66 of the ocular system 60, placed in close proximity to the most proximal surface of the relay optics, causes the image-forming rays to diverge. The image rays are then converged with other ocular surfaces to form the minimally or undistorted final image. Distortion and aberrations are removed with the latter ocular lens surfaces so the observer has a clear image to view.

In most configurations, instead of correcting the image in the objective lens system 30 and the ocular lens system 60 independently of one another, in the preferred endoscope of the present invention the distortions and aberrations are balanced and corrected in the objective lens system, the relay lens system, and the ocular lens system as an integral optical train combination.

Thus, the image transmitted by the ocular lens system to the relay system will typically will contain distortions and aberrations which are ultimately balanced and corrected by the interaction with the optical components of the remainder of the optical train. By removing the conventional limitation that the objective lens system must be independently balanced and corrected, the objective lens system of the invention is optimized to provide the maximum throughput of optical information through the endoscope. This permits better image resolution and improved image brightness, relative to a conventional endoscope in which the objective and ocular systems are independently balanced.

For example, as shown in FIG. 2, in the exemplary embodiments the objective lens system 30 will capture an image and deliver an "unbalanced" image 32 (e.g., curved, enlarging image) through the relay lens system 40, 50 to the ocular lens system 60. At the ocular lens system 60, the aberrations in the image 62 will be compensated for by the integral ocular lens system 60 (FIG. 4) to produce the balanced final image.

Placement of the last image inside glass, as in this ocular embodiment of the invention, instead of in air in close proximity to the first ocular lens also prevents dust and scratches on lens surfaces closely proximal to the image to degrade the final image quality. Embodying the invention in the ocular lens portion of the endoscope may be independent of, or in addition to, the objective-relay embodiment, shown in FIG. 2.

Finally, once the image 62 is produced by the ocular, it can be manipulated in whatever manner is desired. The observer can view the image directly, or can cause the image to impinge—with appropriate magnification as desired—onto on or more CCDs for further image processing.

Referring now to FIGS. 3 and 4, relay 40 along intermediate portion 22 of endoscope 10 will typically comprise one or more relay lens units 50. Relay 40 generally forms an intermediate image 52 in gaps 54 between each pair of adjacent relay lens units 50. Typical endoscopes may include from 1 to about 20 relay units 50, and preferably from about 2 to about 6 relay units. Each unit 50 will preferably comprise a plurality of lenses, preferably including one or more rod lenses to reduce the number of relay units included to transfer the image the desired endoscope shaft length.

Table 1 below specifies the "recipe" or specific individual lenses of an exemplary monoscopic endoscope optical train. This radius, thickness, and diameter (which may be considered arbitrary) measurements in the table are in mm, while the indices of refraction of the lenses are determined by the glasses identified in the associated column. The specified glasses are available from a variety of sources including Schott Optical Glass Inc., of Duryea, Pa., and the listed glass identifiers will be recognized by such suppliers (and others of skill in the art).

TABLE 1

| Surf | Type | Radius | Thickness | Glass | Diameter | Conic |
| --- | --- | --- | --- | --- | --- | --- |
| Obj. | Standard | Infinity | 38 | | 47.38083 | 0 |
| 1. | Standard | Infinity | 0.5 | BK7 | 4 | 0 |
| 2. | Standard | Infinity | 0.2 | | 4 | 0 |

TABLE 1-continued

| Surf | Type | Radius | Thickness | Glass | Diameter | Conic |
|---|---|---|---|---|---|---|
| 3. | Standard | Infinity | 0.5 | SKS | 4 | 0 |
| 4. | Standard | 1.25 | 0.6 | | 2.1 | 0 |
| 5. | Standard | Infinity | 7.07 | BK7 | 2.571 | 0 |
| 6. | Standard | Infinity | 5.75 | LAFN21 | 4 | 0 |
| 7. | Standard | −5.78 | 3.183208 | | 4.8 | 0 |
| 8. | Standard | 6.9 | 3 | FKS | 4.8 | 0 |
| 9. | Standard | −4.227 | 11 | LAFN7 | 4.8 | 0 |
| 10. | Standard | Infinity | 12 | BK7 | 4.8 | 0 |
| 11. | Standard | Infinity | 2.5 | F5 | 4.8 | 0 |
| 12. | Standard | −20.9 | 1.182871 | | 4.6 | 0 |
| 13. | Standard | 23.5 | | LASFN30 | 4.6 | 0 |
| 14. | Standard | Infinity | 43.6 | BK7 | 4.8 | 0 |
| 15. | Standard | −8 | 1 | F5 | 4.8 | 0 |
| 16. | Standard | −16.16 | 0.2 | | 4.599084 | 0 |
| 17. | Standard | Infinity | 0.2 | | 4.597448 | 0 |
| 18. | Standard | 16.16 | 1 | F5 | 4.597832 | 0 |
| 19. | Standard | 8 | 43.6 | BK7 | 4.8 | 0 |
| 20. | Standard | Infinity | 1 | LASFN30 | 4.8 | 0 |
| 21. | Standard | −23.6 | 6 | | 4.6 | 0 |
| 22. | Standard | Infinity | 6 | | 3.95541 | 0 |
| 23. | Standard | 23.5 | 1 | LASFN30 | 4.6 | 0 |
| 24. | Standard | Infinity | 43.6 | BK7 | 4.8 | 0 |
| 25. | Standard | −8 | 1 | F5 | 4.8 | 0 |
| 26. | Standard | −16.16 | 0.2 | | 4.599084 | 0 |
| 27. | Standard | Infinity | 0.2 | | 4.597448 | 0 |
| 28. | Standard | 16.16 | 1 | F5 | 4.597832 | 0 |
| 29. | Standard | 8 | 43.6 | BK7 | 4.8 | 0 |
| 30. | Standard | Infinity | 1 | LASFN30 | 4.8 | 0 |
| 31. | Standard | −23.5 | 6 | | 4.6 | 0 |
| 32. | Standard | Infinity | 6 | | 3.841948 | 0 |
| 33. | Standard | 23.5 | 1 | LASFN30 | 4.6 | 0 |
| 34. | Standard | Infinity | 43.6 | BK7 | 4.8 | 0 |
| 35. | Standard | −8 | 1 | F5 | 4.8 | 0 |
| 36. | Standard | −16.16 | 0.2 | | 4.599084 | 0 |
| 37. | Standard | Infinity | 0.2 | | 4.597448 | 0 |
| 38. | Standard | 16.16 | 1 | F5 | 4.597832 | 0 |
| 39. | Standard | 8 | 43.6 | BK7 | 4.8 | 0 |
| 40. | Standard | Infinity | 1 | LASFN30 | 4.8 | 0 |
| 41. | Standard | −23.5 | 6 | | 4.6 | 0 |
| 42. | Standard | Infinity | 6 | | 3.885353 | 0 |
| 43. | Standard | 23.5 | 1 | LASFN30 | 4.6 | 0 |
| 44. | Standard | Infinity | 43.6 | BK7 | 4.8 | 0 |
| 45. | Standard | −8 | 1 | F5 | 4.8 | 0 |
| 46. | Standard | −16.16 | 0.2 | | 4.599084 | 0 |
| 47. | Standard | Infinity | 0.2 | | 4.597448 | 0 |
| 48. | Standard | 16.16 | 1 | F5 | 4.597832 | 0 |
| 49. | Standard | 8 | 43.6 | BK7 | 4.8 | 0 |
| 50. | Standard | Infinity | 1 | LASFN30 | 4.8 | 0 |
| 51. | Standard | −23.5 | 1 | | 4.8 | 0 |
| 52. | Standard | −12.2 | 2 | FKS | 8 | 0 |
| 53. | Standard | Infinity | 14.5 | BK7 | 8 | 0 |
| 54. | Standard | Infinity | 3 | LF5 | 8 | 0 |
| 55. | Standard | −5.671 | 3.3435 | | 8 | 0 |
| 56. | Standard | −4 | 1.5 | SF6 | 6 | 0 |
| 57. | Standard | Infinity | 0.5 | | 6 | 0 |
| 58. | Standard | Infinity | 2 | LF5 | 8 | 0 |
| 59. | Standard | −13.189 | 8.097363 | | 8 | 0 |
| 60. | Standard | Infinity | 3.5 | BK7 | 10 | 0 |
| 61. | Standard | −11.66 | 3 | | 10 | 0 |
| 62. | Standard | Infinity | 44 | BK7 | 10 | 0 |
| 63. | Standard | Infinity | 1 | | 4.577661 | 0 |
| 64. | Standard | Infinity | 2 | BK7 | 10 | 0 |
| 65. | Standard | Infinity | 7 | | 10 | 0 |

The objective lens system 30 will generally include the lens surfaces up to and including the twelfth numbered surface of Table 1, while the relay 40 will extend from there to the fiftieth numbered surface, as indicated. The proximal group of surfaces includes the ocular lens system 60, as described above. The aperture value is set to twice the first or marginal ray height throughout the chart.

Referring now to FIGS. 5–10, an alternative stereoscopic endoscope optical train 12' generally includes objective 30, relay 40, and ocular 60 lens systems similar to those described above. The stereoscopic optical system comprises two independent but identical optical trains. The enhanced image throughput of the present invention is a particular advantage with these two-channel systems.

One or more of the distal-most lenses 72 of the objective 30, and one or more lenses of ocular 60 proximal of a splitter system 74 may be dedicated to a specific channel of such a stereoscopic system. Nonetheless, a first intermediate image 32 will preferably be contained within a lens of the objective system 30, and a last intermediate image 62 will preferably be contained within a lens 80 of the ocular system 60 as described above. In the exemplary embodiment of the stereoscopic endoscope optical train 12', a novel prism 88 helps to orient one or both of the images. Once again, ocular 60 will typically pass the image on to a camera for display on a monitor (typically using a stereoscopic camera and display system), or binocular eyepieces might be used for direct viewing.

In another aspect, the present invention provides endoscopes having an ocular lens system with independently adjustable lens components. Thus, a user can independently calibrate each channel of a stereoscopic endoscope so as to manipulate the size, location, and orientation of an image of the object while reducing the amount of aberrations introduced into the final image. Both monoscopic and stereoscopic endoscopes need adjustments in diopters and magnification. Additionally, for stereoscopic endoscopes, the images relayed through the left channel and right channel must be stereomatched (e.g., centering images in the X-Y plane) as well as size matched and rotationally matched. Unfortunately, known endoscopes do not allow for independent manipulation of these optical properties of the image. For example, in known ocular assemblies adjustment of one of the optical properties of the image is interrelated with the other optical properties. Consequently, manipulation of one optical property (e.g., magnification) may detrimentally affect the other optical properties (e.g., diopters) and a large amount of aberrations may be introduced into the final displayed image.

The present invention provides monoscopic and stereoscopic endoscopes having an ocular lens system that allows for independent adjustments of the optical properties of the image which also reduces the amount of aberrations introduced into the relayed image. Advantageously, once an adjustment is made to one optical property, subsequent adjustments of the other optical properties of the image do not introduce appreciable changes into the previous adjustments. In most embodiments, all adjustments to the endoscope are done only in the ocular lens system so that the user can focus on the target site without having to adjust the objective lens that is located at a distal end of the endoscope shaft.

In general, each of the lenses of the ocular lens system are disposed within a movable cell that allows a user to rotate and/or axially move the lenses to adjust the properties of the captured image. Some adjustments to the ocular can move the entire ocular lens system, while other adjustments move only selected cells and lenses relative to the rest of the lenses. In exemplary embodiments, the cell and lens components are designed to have a sensitivity that allows users to make fine adjustments to the rotational and axial position of the lenses needed for stereo imaging.

In addition to rotational and axial movement, for stereoscopic endoscopes in particular, some lenses and cells of the ocular system can be moved off of (e.g., orthogonal to) the optical axis. For example, in order to make sure that the images of a right and left ocular system for a stereoscopic endoscope coincide, it is desirable to be able to adjust at least one of the lenses to adjust the X-Y positioning of the one of the channels. By use of the optical train of the present invention, such an adjustment does not appreciably affect the diopters, magnification, and the like. More importantly, however, the adjustment does not introduce appreciable aberrations into the image quality.

Figure 11:
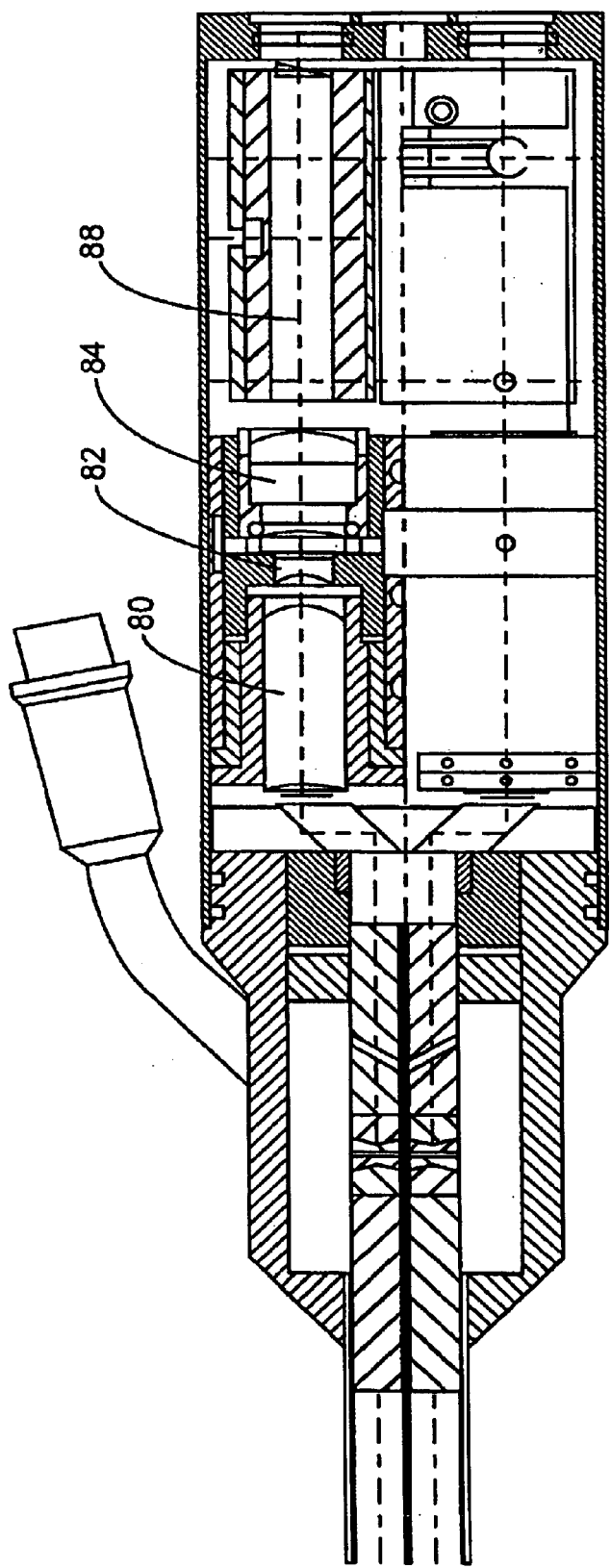
FIG. 11 is a cross-sectional view of an ocular lens system inside the scope body.

As illustrated in FIGS. 10 and 11, the endoscope comprises an elongate shaft 72 having a distal portion (not shown), an intermediate portion 74, and a proximal portion 76 that houses the ocular system.

In use, the distal portion of the endoscope is inserted into a body cavity to position an objective lens system (FIGS. 1 and 2) into close proximity of the target object O. The objective lens system, relay system 78, and ocular lens system 60 are positioned within an optical path within the endoscope such that an image of the object can be transmitted to a camera 24 that is optically coupled to the proximal end 16 of the endoscope (FIG. 1). Camera 24 will typically have a charge-couple device (CCD) or the like, so that the camera can transmit image signals to allow a display D to reproduce the image O'. Once the image is relayed through the objective lens system 30 and relay lens system 40 the image is processed by the ocular lens system 60.

An exemplary embodiment of the ocular lens system 60 is shown in detail in FIGS. 10 and 11. Each side of the stereoscopic ocular lens system 60 includes a first lens 80, a second lens 82, a third lens 84, a fourth lens 86, and a prism 88 aligned with an optical axis 89 of that side of the endoscope. The lenses can be single or compound lenses. The lenses are disposed within moveable cells 90, 92, 94, 96 which can be rotatable, moveable along the optical axis 89 and/or moveable off of (orthogonal to) the optical axis. As noted above, most embodiments of the endoscope comprise a fixed objective lens system and a fixed relay system so that all manipulation of the image is done in the proximal ocular lens system 60.

In the illustrated configuration, the first lens 80 is a positive rod lens where the last relay unit forms the image 62 inside this rod lens 80. Similar to above, by forming the image within the lens, dust and other particles are prevented from degrading the image quality. Lens 82 is a negative lens, and as will be described below, can be moved off the optical axis 89 to adjust the X-Y positioning of the image. Lens 84 and lens 86 are positive singlet or compound lenses. Prism 88 is typically a dove prism or Abbe Konig prism. It should be appreciated, however, that other lens combinations are within the scope of the present invention.

Figure 12:
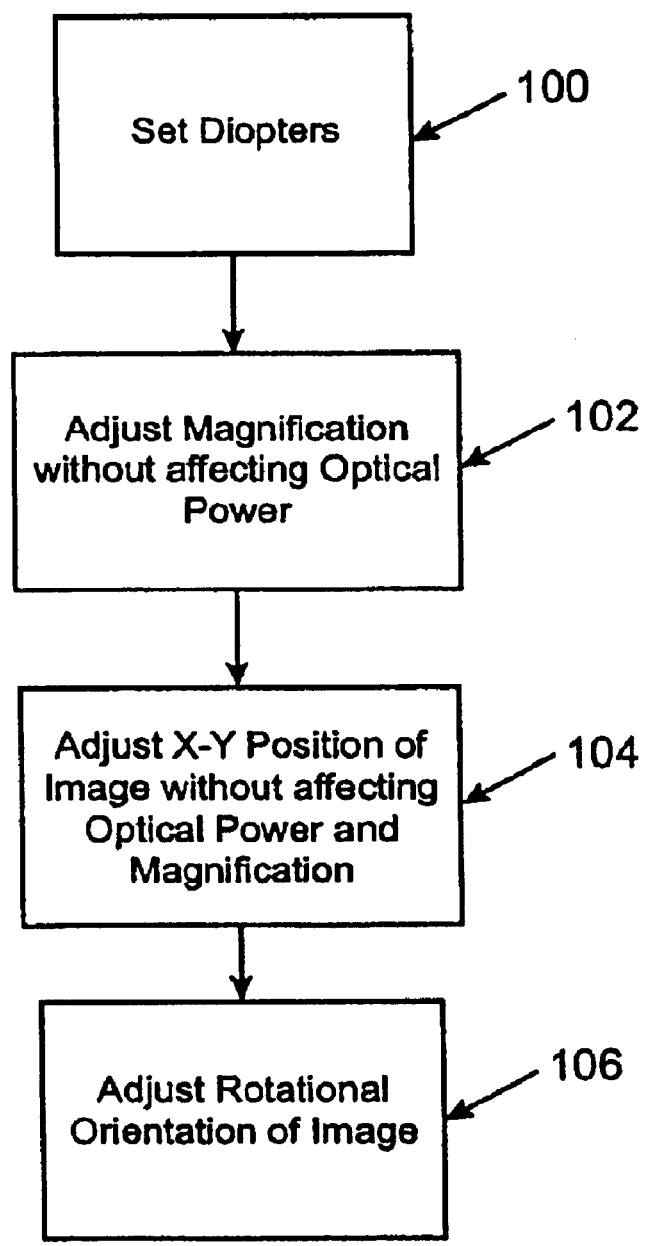
FIG. 12 is a simplified flow chart illustrating one exemplary method of adjustments for the present invention.
Figure 13A:
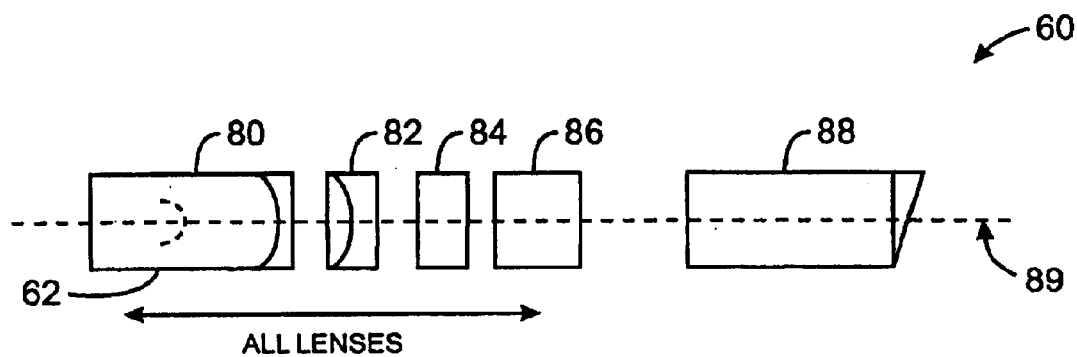
FIGS. 13A–13D schematically illustrates the relative movement of the lenses and prism.
Figure 13B:
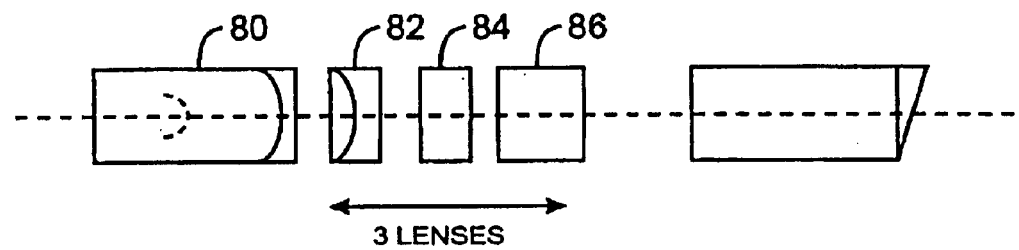
Figure 13C:
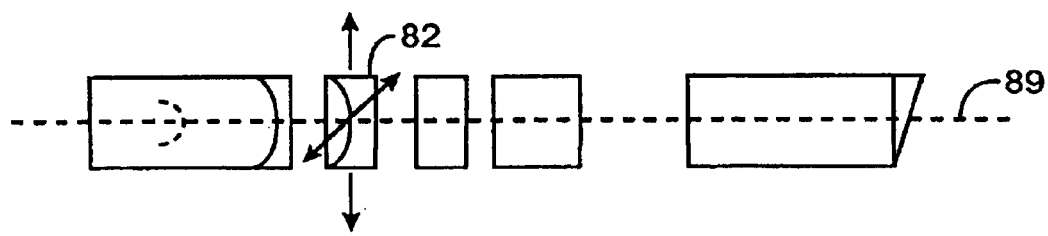
Figure 13D:
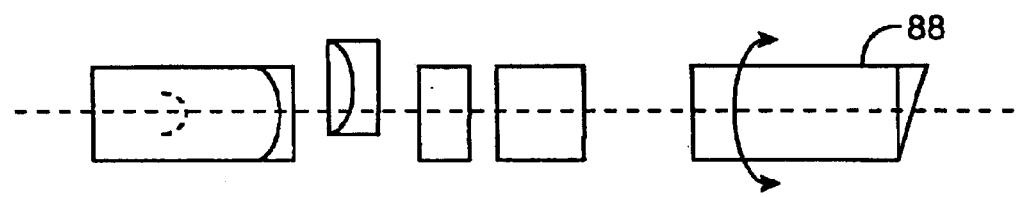

In the exemplary methods illustrated in FIGS. 12 and 13A–13D, the ocular lens system 60 can be adjusted to manipulate the displayed image. As shown in FIGS. 12 and 13A, the image 62 is formed within lens 80 and all of the lenses and cells are moved axially, relative to the image position to adjust the diopters (Step 100). Once the diopters has been set, the cell containing all the lenses 80, 82, 84, 86 is locked into position.

Magnification of the image is adjusted by moving lenses 82, 84, 86 relative to the now stationary lens 80 (Step 102). Consequently, the diopters of the ocular system is maintained while lenses 82, 84, 86 are moved axially until the desired magnification has been achieved. Thereafter, the lenses 82, 84, 86 are locked in their axial position. If it is later desired to adjust magnification, the lenses 82, 84, 86 can be unlocked and moved axially to increase or decrease the magnification.

For stereoscopic endoscopes, it is further desirable to adjust the X-Y positioning of the image so that the images from the left and right optical assemblies coincide by the stereo view of the images (Step 104). To change the X-Y positioning of the image, lens 82 can be moved off the optical axis 89. Applicants have found that in this embodiment, moving the negative lens (instead of the positive lens) introduces the least amount of aberrations into the image. While the positive lens—negative lens—positive lens configuration is the preferred lens structure, it will be appreciated that other lens configurations are possible. For example, in an alternative embodiment, negative lens 82 and positive lenses 84, 86 can be coupled together and the entire combination of lenses can be moved off of the optical axis to change X-Y positioning. However, such a combination does not provide the same image quality of the ocular system in which only lens 82 is moved orthogonally.

To control the rotational orientation of the image in the left and right ocular assemblies, the prism 88 can be rotated until the desired image orientation is achieved (Step 106). The prism is typically a dove prism, an Abbe Konig prism, or the like. In an exemplary configuration, one degree of rotation of the prism 88 can rotate the image by two degrees.

For stereoscopic endoscopes, the position and orientation of the lenses disposed within the left and right channels should be independently adjustable to allow the user to calibrate and "stereo match" the channels.

In yet another aspect, the present invention provides a device for adjusting the stereo line of convergence between the two optical channels. In an exemplary embodiment, the present invention sets the stereo line of convergence that is 50 mm from the distal tip of the stereoscopic endoscope. While the following discussion focuses on the exemplary embodiment, it should be appreciated that the concepts of the present invention can be modified to work with endoscopes having other working distances.

Figure 14A:
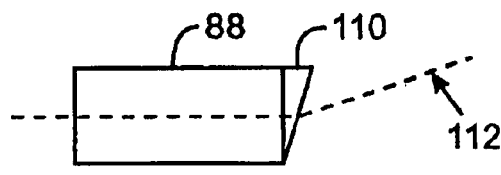
FIGS. 14A and 14B show a wedge disposed on the proximal end of the prism.
Figure 14B:
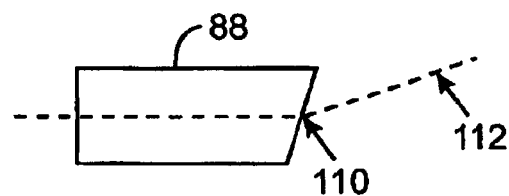

As shown in FIGS. 11, 14A and 14B, in order to set the stereo line of convergence, a wedge 110 is used to offset the light rays 112 through the proximal end of prism 88. Wedge 10 can be added onto the proximal end of the dove prism or Abbe Konig prism to refract the light 112 to create the stereo line convergence (FIG. 14A). Alternatively, the proximal end of the prism 88 can be shaped to form the proximal, angled, wedge surface (FIG. 14B). While not shown, the wedges 10 in the two channels will mirror each other across the longitudinal axis of the stereo endoscope.

To create the stereo line of convergence, it is possible to move the whole ocular lens system. Unfortunately, movement of the entire ocular introduces aberrations into the image and degrades the quality of the image. Applicants have found that addition of the wedge to the proximal end of the prism provides an improved image quality with reduced aberrations, while reducing the cost of manufacturing of the ocular lens system.

Figure 15:
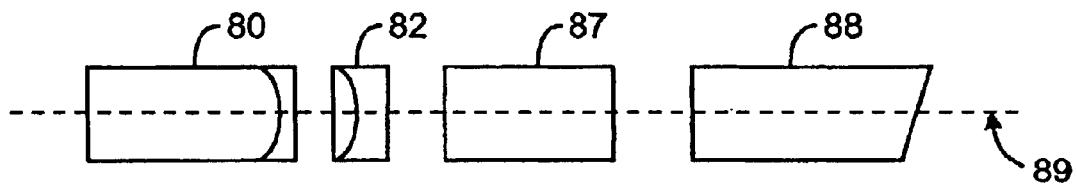
FIGS. 15–18 schematically illustrate alternative ocular system embodiments of the present invention.
Figure 16:
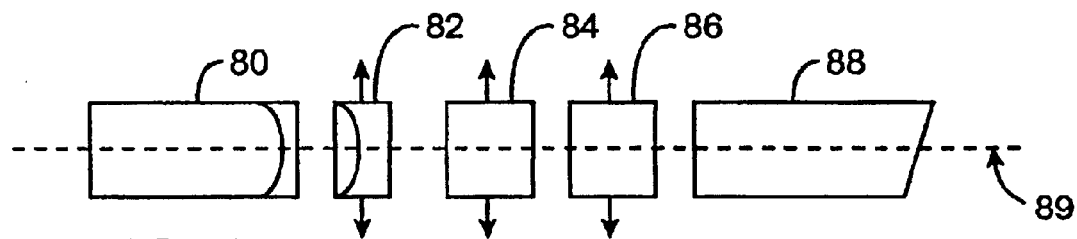
Figure 17:
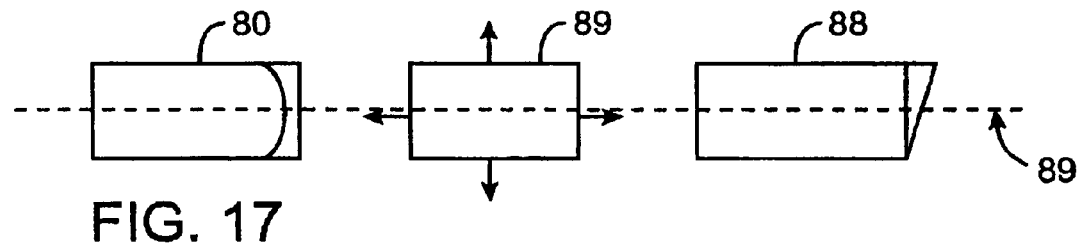
Figure 18:
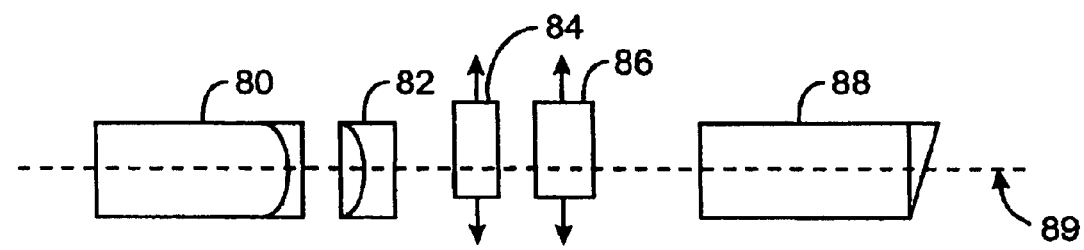

While the exemplary embodiments have been described in some detail, by way of example and for clarity of understanding, a variety of changes, adaptations, and modifications will be obvious to those of skill in the art. For example, since lenses 84 and 86 move together, it may be possible to combine lenses 84, 86 into one integral compound lens 87 (FIG. 15). In another alternative embodiment, instead of moving only lens 82 to adjust the X-Y positioning of the image, lenses 82, 84, 86 can all be moved orthogonal to the optical axis (FIG. 16). Similarly, it may be possible to integrate lens 82, 84, and 86 into a single lens 89 that is axially moveable and orthogonally moveable so that the single lens can be moved to control magnification and X-Y positioning (FIG. 17). In yet another alternative embodiment, it may even be possible to leave lens 82 within the optical path and move lens 84 and/or 86 orthogonally to adjust the X-Y positioning of the image (FIG. 18). Unfortunately, the above described alternatives, while viable, introduce additional aberrations into the image.

It should be appreciated that for monoscopic endoscopes, it is typically only necessary to adjust the diopters and magnification of the image. Consequently, the methods of the present invention may only require adjustment of the diopters (step 100) and adjustment of magnification (step 102). Accordingly, the scope of the present invention is limited solely by the appended claims.

What is claimed is:

1. An optical train for viewing an object, the optical train comprising:
   an objective lens system for capturing an image of the object;
   an ocular lens system that forms a final image of the object;
   a relay lens system disposed along an optical path between the objective lens system and the ocular lens system;
   wherein an intermediate image is formed within an optical element in the ocular lens system,
   wherein the relay lens system is separated from the ocular lens system by an ocular-relay gap, wherein the optical element is disposed adjacent the relay lens system, and wherein no intermediate image is disposed within the ocular-relay gap.

2. The optical train of claim 1 wherein the optical element has an index of refraction greater than one.

3. The optical train of claim 1 wherein the intermediate image formed within the optical element is expanding.

4. The optical train of claim 1 wherein the optical element comprises a single lens, a rod lens, a compound lens, an extended lens, or a glass element.

5. The optical train of claim 1 wherein the optical element comprises a glass element coupled to a lens, wherein the intermediate image is formed in the glass element.

6. The optical train of claim 1 wherein the relay lens system is separated from the objective lens system by an objective-relay gap, and wherein no intermediate image is disposed within the objective-relay gap.

7. An endoscope comprising:
   a shaft having a distal portion adjacent a distal end and a proximal portion adjacent a proximal end;
   an ocular lens system disposed along the proximal portion;
   a relay lens system disposed along the shaft between the proximal portion and the distal portion;
   an objective lens system disposed along the distal portion, the objective lens system comprising a lens, the objective lens system forming a first intermediate image within the lens;
   wherein the relay lens system comprises a plurality of axially separated relay units, the relay units being interchangeable and each relay unit comprising an axially symmetric set of relay lenses, wherein a relay gap is disposed between each pair of adjacent relay units so that an associated relay intermediate image is formed therein.

8. The endoscope of claim 7 wherein the ocular lens system comprises a second lens, wherein the relay lens system is separated from the ocular lens system by an ocular-relay gap, wherein the second lens is disposed adjacent the relay lens system, and wherein no intermediate image is disposed within the ocular-relay gap.

9. The endoscope of claim 7 wherein the relay lens system is separated from the objective lens system by an objective-relay gap, wherein the lens is disposed adjacent the relay lens system, and wherein no intermediate image is disposed within the objective-relay gap.

10. An endoscope comprising:
    a shaft having a distal portion adjacent a distal end and a proximal portion adjacent a proximal end;
    an objective lens system disposed along the distal portion;
    an ocular lens system disposed along the proximal portion, the ocular lens system comprising a lens;
    a relay lens system disposed along the shaft between the objective lens system and the ocular lens system, wherein the relay lens system is separated from the objective lens system by an objective-relay gap and the relay lens system is separated from the ocular lens system by an ocular-relay gap,
    wherein intermediate image(s) are formed in at least one of the objective lens system, ocular lens system and relay lens system, and wherein no intermediate image is formed in the objective-relay gap and the ocular-relay gap.

11. The endoscope of claim 10, wherein the intermediate images are formed separately in the objective lens system, the ocular system and the relay lens system.

12. The endoscope of claim 10, wherein the intermediate image is formed in the ocular system.

13. The endoscope of claim 10, wherein the relay lens system comprises a plurality of axially separated relay units, the relay units being interchangeable and each relay unit comprising an axially symmetric set of relay lenses, wherein a relay gap is disposed between each pair of adjacent relay units so that an associated relay intermediate image is formed therein.

14. The endoscope of claim 10, wherein the relay lens system comprises a plurality of axially separated relay units, the relay units being interchangeable and each relay unit comprising an axially symmetric set of relay lenses, wherein an optical element is disposed between each pair of adjacent relay units so that an intermediate image is formed in the optical element.

15. The endoscope of claim 14, wherein the optical element has a refractive index greater than one.

16. An endoscope comprising:
    a shaft having a distal portion adjacent a distal end and a proximal portion adjacent a proximal end;
    an objective lens system disposed along the distal portion;
    an ocular lens system disposed along the proximal portion, the ocular lens system comprising a lens; and
    a relay lens system disposed along the shaft between the objective lens system and the ocular lens system,
    wherein an intermediate image is formed in the lens in the ocular lens system.

17. The endoscope of claim 16, wherein the relay lens system is separated from the objective lens system by an objective-relay gap and the relay lens system is separated from the ocular lens system by an ocular-relay gap.

18. The endoscope of claim 17, wherein no intermediate image is formed in the ocular-relay gap.

19. The endoscope of claim 17, wherein no intermediate image is formed in the objective-relay gap.

20. An optical train for viewing an object, the optical train comprising:

an objective lens system for capturing an image of the object;

an ocular lens system that forms a final image of the object;

a relay lens system disposed along an optical path between the objective lens system and the ocular lens system;

wherein an intermediate image is formed within an optical element in the ocular lens system, wherein the relay lens system is separated from the ocular lens system by an ocular-relay gap, wherein the optical element is disposed adjacent the relay lens system, and wherein no intermediate image is disposed within the ocular-relay gap.

21. The optical train of claim 20 wherein the optical element has an index of refraction greater than one.

22. The optical train of claim 20 wherein the intermediate image formed within the optical element is expanding.

23. The optical train of claim 20 wherein the optical element comprises a single lens, a rod lens, a compound lens, an extended lens, or a glass element.

24. The optical train of claim 20 wherein the optical element comprises a glass element coupled to a lens, wherein the intermediate image is formed in the glass element.

25. An endoscope comprising:

a shaft having a distal portion adjacent a distal end and a proximal portion adjacent a proximal end;

an ocular lens system disposed along the proximal portion;

a relay lens system disposed along the shaft between the proximal portion and the distal portion;

an objective lens system disposed along the distal portion, the objective lens system comprising a lens, the objective lens system forming a first intermediate image within the lens;

wherein the relay lens system is separated from the objective lens system by an objective-relay gap, wherein the lens is disposed adjacent the relay lens system, and wherein no intermediate image is disposed within the objective-relay gap; and wherein the ocular lens system comprises a second lens, wherein the relay lens system is separated from the ocular lens system by an ocular-relay gap, wherein the second lens is disposed adjacent the relay lens system, and wherein no intermediate image is disposed within the ocular-relay gap.

26. An endoscope comprising:

a shaft having a distal portion adjacent a distal end and a proximal portion adjacent a proximal end;

an ocular lens system disposed along the proximal portion;

a relay lens system disposed along the shaft between the proximal portion and the distal portion;

an objective lens system disposed along the distal portion, the objective lens system comprising a lens, the objective lens system forming a first intermediate image within the lens;

wherein the ocular lens system comprises a second lens, wherein the relay lens system is separated from the ocular lens system by an ocular-relay gap, wherein the second lens is disposed adjacent the relay lens system, and wherein no intermediate image is disposed within the ocular-relay gap; and wherein the relay lens system comprises a plurality of axially separated relay units, the relay units being interchangeable and each relay unit comprising an axially symmetric set of relay lenses, wherein a relay gap is disposed between each pair of adjacent relay units so that an associated relay intermediate image is formed therein.

27. An endoscope comprising:

a shaft having a distal portion adjacent a distal end and a proximal portion adjacent a proximal end;

an ocular lens system disposed along the proximal portion;

a relay lens system disposed along the shaft between the proximal portion and the distal portion;

an objective lens system disposed along the distal portion, the objective lens system comprising a lens, the objective lens system forming a first intermediate image within the lens;

wherein the relay lens system is separated from the objective lens system by an objective-relay gap, wherein the lens is disposed adjacent the relay lens system, and wherein no intermediate image is disposed within the objective-relay gap; and wherein the relay lens system comprises a plurality of axially separated relay units, the relay units being interchangeable and each relay unit comprising an axially symmetric set of relay lenses, wherein a relay gap is disposed between each pair of adjacent relay units so that an associated relay intermediate image is formed therein.

28. An endoscope comprising:

a shaft having a distal portion adjacent a distal end and a proximal portion adjacent a proximal end;

an ocular lens system disposed along the proximal portion;

a relay lens system disposed along the shaft between the proximal portion and the distal portion;

an objective lens system disposed along the distal portion, the objective lens system comprising a lens, the objective lens system forming a first intermediate image within the lens;

wherein the relay lens system is separated from the objective lens system by an objective-relay gap, wherein the lens is disposed adjacent the relay lens system, and wherein no intermediate image is disposed within the objective-relay gap; and wherein the relay lens system comprises a plurality of axially separated relay units, the relay units being interchangeable and each relay unit comprising an axially symmetric set of relay lenses, wherein an optical element is disposed between each pair of adjacent relay units so that intermediate image is formed in the optical element.

29. The endoscope of claim 28, wherein the optical element has a refractive index greater than one.

30. The endoscope of claim 28, wherein the ocular lens system comprises a second lens, wherein the relay lens system is separated from the ocular lens system by an ocular-relay, wherein the second lens is disposed adjacent the relay lens system, and wherein no intermediate image is disposed within the ocular-relay gap.

* * * * *

UNITED STATES PATENT AND TRADEMARK OFFICE
CERTIFICATE OF CORRECTION

PATENT NO. : 6,817,975 B1
DATED : November 16, 2004
INVENTOR(S) : Mina Farr and Wolfgang Braxmeir It is certified that error appears in the above-identified patent and that said Letters Patent is hereby corrected as shown below:

Column 18,
Line 63, after "ocular-relay" add the word -- gap, --

Signed and Sealed this

First Day of February, 2005

JON W. DUDAS
*Director of the United States Patent and Trademark Office*